US011285260B2

(12) United States Patent
Cole

(10) Patent No.: US 11,285,260 B2
(45) Date of Patent: Mar. 29, 2022

(54) BUTTON SAFETY CAP FOR CATHETER INSERTION DEVICE

(71) Applicant: Becton, Dickinson and Company, Franklin Lakes, NJ (US)

(72) Inventor: Russell Cole, River Vale, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 399 days.

(21) Appl. No.: 15/567,544

(22) PCT Filed: Apr. 20, 2016

(86) PCT No.: PCT/US2016/028398
§ 371 (c)(1),
(2) Date: Oct. 18, 2017

(87) PCT Pub. No.: WO2016/172182
PCT Pub. Date: Oct. 27, 2016

(65) Prior Publication Data
US 2018/0099087 A1  Apr. 12, 2018

Related U.S. Application Data

(60) Provisional application No. 62/152,587, filed on Apr. 24, 2015.

(51) Int. Cl.
*A61M 5/142* (2006.01)
*A61M 5/32* (2006.01)
*A61M 5/158* (2006.01)

(52) U.S. Cl.
CPC ........ *A61M 5/14248* (2013.01); *A61M 5/158* (2013.01); *A61M 5/3202* (2013.01);
(Continued)

(58) Field of Classification Search
CPC ............ A61M 5/31571; A61M 5/3202; A61M 5/3204; A61M 2005/14252;
(Continued)

(56) References Cited

U.S. PATENT DOCUMENTS 4,484,910 A * 11/1984 Sarnoff ............... A61M 5/2033
604/136
5,085,641 A * 2/1992 Sarnoff ............... A61M 5/2033
604/134
(Continued)

FOREIGN PATENT DOCUMENTS

CN  201270215 Y  7/2009
CN  104474604 A  4/2015
(Continued)

OTHER PUBLICATIONS

Chinese Office Action dated Nov. 22, 2019, which issued in the corresponding Chinese Patent Application No. 201680030885.7, including English translation.
(Continued)

*Primary Examiner* — Kami A Bosworth
(74) *Attorney, Agent, or Firm* — Dickinson Wright PLLC

(57) ABSTRACT

A button safety cap for a patch pump or other fluid infusion device prevents accidental activation of an activation button of a catheter insertion device. The button safety cap includes a stabilizing surface adapted to stabilize the patch pump when the patch pump is oriented for filling a reservoir port.

9 Claims, 16 Drawing Sheets

(52) U.S. Cl.
CPC ............. *A61M 2005/14252* (2013.01); *A61M 2205/276* (2013.01)

(58) Field of Classification Search
CPC ........... A61M 2005/14256; A61M 2005/1585; A61M 2005/206; A61M 2005/2073; A61M 2205/27; A61M 2205/276; A61M 5/14248

See application file for complete search history.

(56) References Cited

U.S. PATENT DOCUMENTS

| | | | |
|---|---|---|---|
| 6,210,369 B1* | 4/2001 | Wilmot | A61M 5/2033 604/157 |
| 7,648,483 B2* | 1/2010 | Edwards | A61M 5/19 604/140 |
| 7,762,992 B2 | 7/2010 | Triplett et al. | |
| 7,988,660 B2 | 8/2011 | Byland et al. | |
| 8,512,287 B2 | 8/2013 | Cindrich et al. | |
| 8,998,851 B2 | 4/2015 | Constantineau et al. | |
| 9,808,582 B2* | 11/2017 | Kramer | A61M 5/2066 |
| 2003/0229308 A1* | 12/2003 | Tsals | A61M 5/20 604/116 |
| 2004/0002682 A1* | 1/2004 | Kovelman | A61M 5/158 604/136 |
| 2004/0116847 A1* | 6/2004 | Wall | A61K 9/0019 604/93.01 |
| 2007/0093760 A1* | 4/2007 | Wexler | A61B 17/0057 604/187 |
| 2008/0059133 A1* | 3/2008 | Edwards | G06Q 10/00 703/7 |
| 2008/0228147 A1* | 9/2008 | David-Hegerich | A61M 5/326 604/198 |
| 2009/0240240 A1* | 9/2009 | Hines | A61M 5/14248 604/890.1 |
| 2011/0144594 A1* | 6/2011 | Sund | A61M 5/2033 604/228 |
| 2011/0160696 A1 | 6/2011 | Hoss | |
| 2012/0302964 A1* | 11/2012 | MacDonald | A61M 5/3155 604/189 |
| 2013/0046239 A1* | 2/2013 | Gonnelli | A61M 5/14248 604/135 |
| 2013/0060233 A1 | 3/2013 | O'Connor et al. | |
| 2014/0163526 A1* | 6/2014 | Cabiri | A61M 5/3287 604/513 |
| 2015/0080799 A1* | 3/2015 | Schneider | A61M 5/14248 604/151 |
| 2016/0296716 A1* | 10/2016 | Cabiri | A61M 5/5086 |

FOREIGN PATENT DOCUMENTS

| | | |
|---|---|---|
| JP | 2003158563 A | 5/2003 |
| JP | 2013507230 A | 3/2013 |
| WO | 2015038850 A2 | 3/2015 |

OTHER PUBLICATIONS

International Search Report dated Jul. 26, 2016 which issued in Application No. PCT/US2016/028398.

Japanese Office Action dated Mar. 10, 2020, which issued in the corresponding Japanese Patent Application No. 2017-555560, including English translation.

Chinese Office Action dated Jul. 15, 2020, which issued in the corresponding Chinese Patent Application No. 201680030885.7, including English translation.

* cited by examiner

BUTTON SAFETY CAP FOR CATHETER INSERTION DEVICE

FIELD OF THE INVENTION

The present invention is directed to a catheter insertion device and to a fluid infusion device including the catheter insertion device. More particularly, the present invention is directed to a button safety cap for preventing accidental deployment of the catheter, and to provide a stable configuration for filling a reservoir of the fluid infusion device.

BACKGROUND OF THE INVENTION

Diabetes is a group of diseases characterized by high levels of blood glucose resulting from the inability of diabetic patients to maintain proper levels of insulin production when required. Persons with diabetes may require some form of daily insulin therapy to maintain control of their glucose levels. Diabetes can be dangerous to the affected patient if it is not treated, and it can lead to serious health complications and premature death. However, such complications can be minimized by utilizing one or more treatment options to help control the diabetes and reduce the risk of complications.

The treatment options for diabetic patients include specialized diets, oral medications and/or insulin therapy. The main goal of diabetes treatment is to control the diabetic patient's blood glucose or sugar level. However, maintaining proper diabetes management may be complicated because it has to be balanced with the activities of the diabetic patient.

For the treatment of type 1 diabetes, there are two principal methods of daily insulin therapy. In the first method, diabetic patients use syringes or insulin pens to self-inject insulin when needed. This method requires the needle stick for each injection, and the diabetic patient may require three to four injections daily. The syringes and insulin pens that are used to inject insulin are relatively simple to use and cost effective.

Another effective method for insulin therapy and managing diabetes is infusion therapy or infusion pump therapy in which an insulin pump is used. The insulin pump can provide continuous infusion of insulin to a diabetic patient at varying rates in order to more closely match the functions and behavior of a properly operating pancreas of a non-diabetic person that produces the required insulin, and the insulin pump can help the diabetic patient maintain his/her blood glucose level within target ranges based on the diabetic patient's individual needs.

Infusion pump therapy requires an infusion cannula, typically in the form of an infusion needle or a flexible catheter, that pierces the diabetic patient's skin and through which, infusion of insulin takes place. Infusion pump therapy offers the advantages of continuous infusion of insulin, precision dosing, and programmable delivery schedules.

In infusion therapy, insulin doses are typically administered at a basal rate and in a bolus dose. When insulin is administered at a basal rate, insulin is delivered continuously over 24 hours in order to maintain the diabetic patient's blood glucose levels in a consistent range between meals and rest, typically at nighttime. Insulin pumps may also be capable of programming the basal rate of insulin to vary according to the different times of the day and night. In contrast, a bolus dose is typically administered when a diabetic patient consumes a meal, and generally provides a single additional insulin injection to balance the consumed carbohydrates. Insulin pumps may be configured to enable the diabetic patient to program the volume of the bolus dose in accordance with the size or type of the meal that is consumed by the diabetic patient. In addition, insulin pumps may also be configured to enable the diabetic patient to infuse a correctional or supplemental bolus dose of insulin to compensate for a low blood glucose level at the time when the diabetic patient is calculating the bolus dose for a particular meal that is to be consumed.

Insulin pumps advantageously deliver insulin over time rather than in single injections, typically resulting in less variation within the blood glucose range that is recommended. In addition, insulin pumps may reduce the number of needle sticks which the diabetic patient must endure, and improve diabetes management to enhance the diabetic patient's quality of life.

Typically, regardless of whether a diabetic patient uses multiple daily injections (MDIs) or a pump, the diabetic patient takes fasting blood glucose medication (FBGM) upon awakening from sleep, and also tests for glucose in the blood during or after each meal to determine whether a correction dose is required. In addition, the diabetic patient may test for glucose in the blood prior to sleeping to determine whether a correction dose is required, for instance, after eating a snack before sleeping.

To facilitate infusion therapy, there are generally two types of insulin pumps, namely, conventional pumps and patch pumps. Conventional pumps require the use of a disposable component, typically referred to as an infusion set, tubing set or pump set, which conveys the insulin from a reservoir within the pump into the skin of the user. The infusion set consists of a pump connector, a length of tubing, and a hub or base from which a cannula, in the form of a hollow metal infusion needle or flexible plastic catheter extends. The base typically has an adhesive that retains the base on the skin surface during use. The cannula can be inserted onto the skin manually or with the aid of a manual or automatic insertion device. The insertion device may be a separate unit required by the user.

Another type of insulin pump is a patch pump. Unlike a conventional infusion pump and infusion set combination, a patch pump is an integrated device that combines most or all of the fluidic components, including the fluid reservoir, pumping mechanism and mechanism for automatically inserting the cannula, in a single housing which is adhesively attached to an infusion site on the patient's skin, and does not require the use of a separate infusion or tubing set. A patch pump containing insulin adheres to the skin and delivers the insulin over a period of time via an integrated subcutaneous cannula. Some patch pumps may wirelessly communicate with a separate controller device (as in one device sold by Insulet Corporation under the brand name OmniPod®), while others are completely self-contained. Such devices are replaced on a frequent basis, such as every three days, when the insulin reservoir is exhausted or complications may otherwise occur, such as restriction in the cannula or the infusion site.

As patch pumps are designed to be a self-contained unit that is worn by the diabetic patient, it is preferable to be as small as possible so that it does not interfere with the activities of the user. Thus, in order to minimize discomfort to the user, it would be preferable to minimize the overall thickness of the patch pump. However, in order to minimize the thickness of the patch pump, its constituent parts should be reduced as much as possible. One such part is the insertion mechanism for automatically inserting the cannula into the user's skin.

In some patch pumps, there is an activation button that triggers deployment of the catheter. Such patch pumps also include a fill port for filling a reservoir of the patch pump with insulin, or the like. One problem with button-based catheter insertion mechanisms is accidental pressing of the activation button. In particular, if the fill port is on the bottom of the pump or other medication delivery device, a user may turn the device upside down and rest it on a surface while they inject fluid into the fill port. This action risks the user accidentally causing the button to be pressed. Furthermore, if the deployment button is on the top of the device, and the user turns the device over to fill the reservoir, the pre-activation button may present an unstable configuration for resting the device on a surface while filling the reservoir.

Accordingly, a need exists for an improved insertion mechanism that includes a button safety feature or device to prevent accidental activation of the catheter insertion device, and to provide a stable configuration for filling the reservoir.

SUMMARY OF THE INVENTION

The present invention is directed to a button safety cap for a catheter insertion device. The button safety cap comprises a pull member, at least one stabilizing arm adapted to prevent rotation and/or translation of the button safety cap relative to the activation button and/or a patch pump or other medication delivery device upon which the button safety cap is assembled, and a flexible snap feature adapted to engage an activation button of the patch pump. The snap feature retains the button safety cap on the patch pump until a predetermined removal force is applied to the button safety cap.

These and other aspects of the invention will become apparent from the following detailed description of the invention which, taken in conjunction with the annexed drawings, show various embodiments of the invention.

BRIEF DESCRIPTION OF THE DRAWINGS

The various objects, advantages and novel features of the illustrative embodiments of the present invention will be more readily appreciated from the following detailed description when read in conjunction with the appended drawings, in which.

Throughout the drawings it will be understood that like reference numbers refer to like features and structures.

DETAILED DESCRIPTION OF ILLUSTRATIVE EMBODIMENTS OF THE INVENTION

Figure 1:
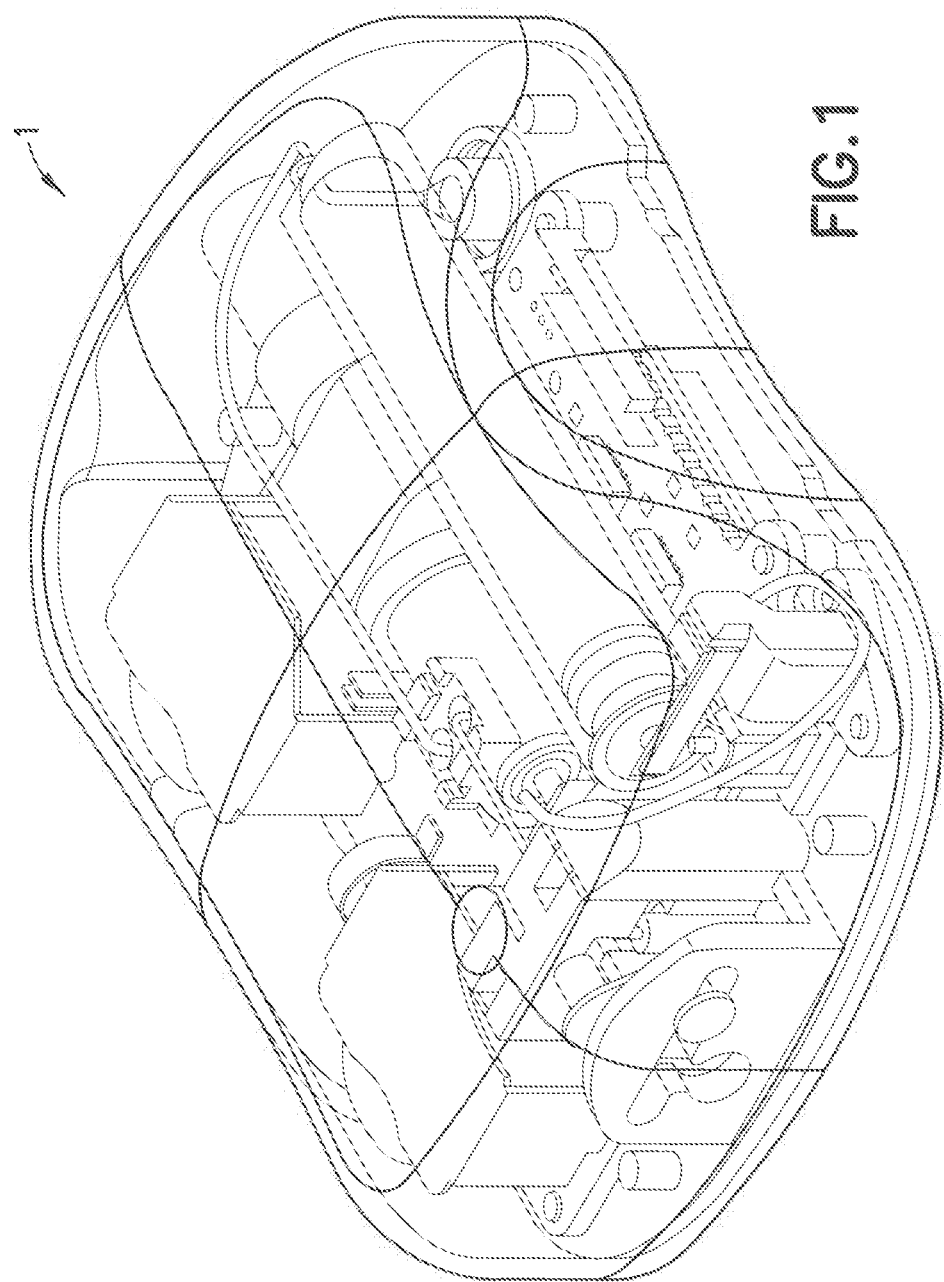
FIG. 1 is a perspective view of a patch pump incorporating a low-profile cannula insertion device, illustrated with a transparent cover for clarity.
Figure 2:
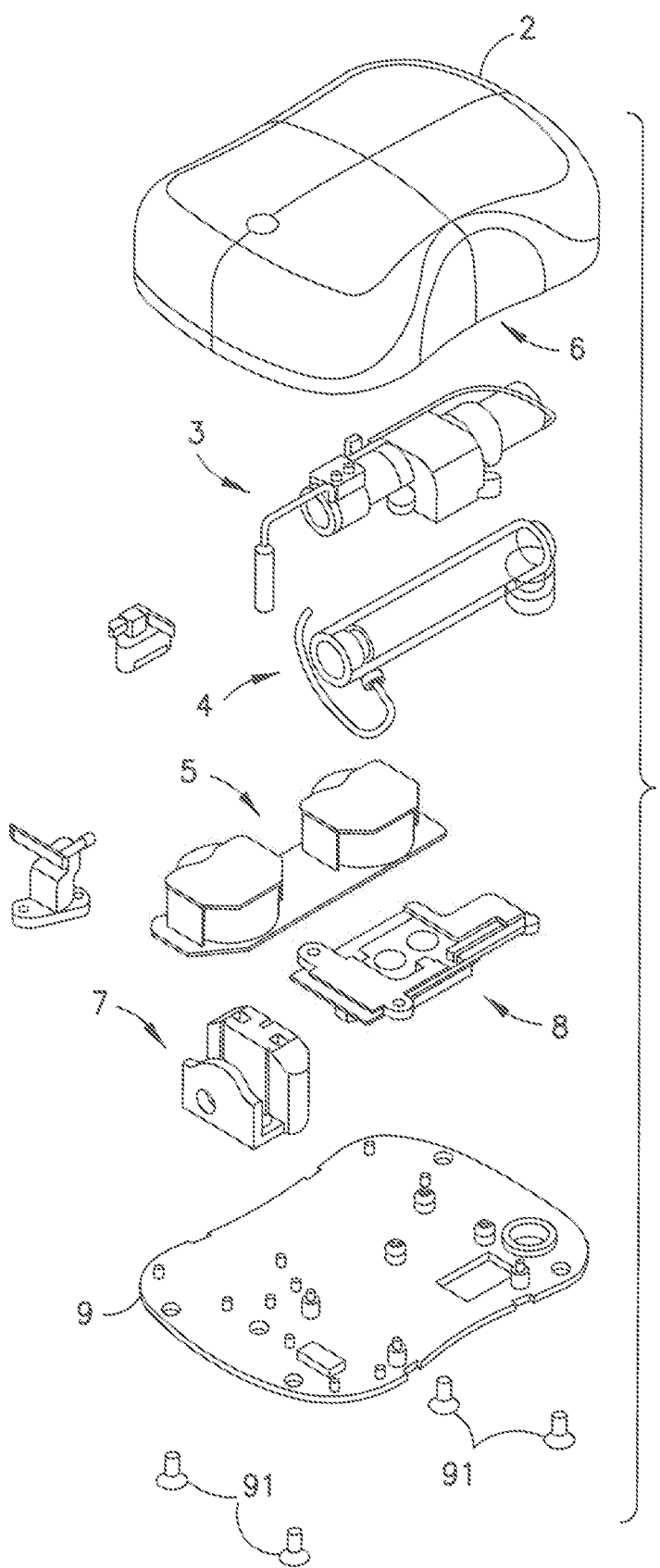
FIG. 2 is an exploded view of the various components of the patch pump of FIG. 1, illustrated with a cover.

FIG. 1 is a perspective view of an illustrative embodiment of a patch pump 1 according to an illustrative embodiment of the invention. The patch pump 1 is illustrated with a see-through cover for clarity and illustrates various components that are assembled to form the patch pump 1. FIG. 2 is an exploded view of the various components of the patch pump of FIG. 1, illustrated with a solid cover 2. The various components of the patch pump 1 may include: a reservoir 4 for storing insulin; a pump 3 for pumping insulin out of the reservoir 4; a power source 5 in the form of one or more batteries; an insertion mechanism 7 for inserting an inserter needle with a catheter into the user's skin; control electronics 8 in the form of a circuit board with optional communications capabilities to outside devices such as a remote controller and computer, including a smart phone; a dose button 6 on the cover 2 for actuating an insulin dose, including a bolus dose; and a base 9 to which various components above may be attached via fasteners 91. The patch pump 1 also includes various fluid connector lines that transfer insulin pumped out of the reservoir 4 to the infusion site.

It should be understood that inserter mechanisms come in various configurations. In some embodiments, the inserter mechanism inserts a soft catheter into the skin. In these embodiments, typically the soft catheter is supported on a rigid insertion needle. The insertion needle is inserted into the skin along with the soft catheter, and then retracted from the skin, leaving the soft catheter in the skin. In other embodiments, a soft catheter is not provided, and the insertion needle remains in the skin and forms a portion of the insulin flow path to deliver insulin until the infusion is finished. Insertion needles are typically hollow, and need to be hollow if they form part of the insulin flow path. However, insertion needles that support a soft catheter and then retract may be solid or hollow. If the insertion needle deploys a soft catheter, and retracts but remains part of the insulin flow path, then the insertion needle should be hollow. However, if the insertion needle deploys a soft catheter and then retracts but does not form part of the insulin flow path, then the insertion needle may be solid or hollow. In either case, the insertion needle is preferably rigid enough to reliably penetrate the skin, but otherwise may be made flexible enough to provide comfort to the user.

Figure 3:
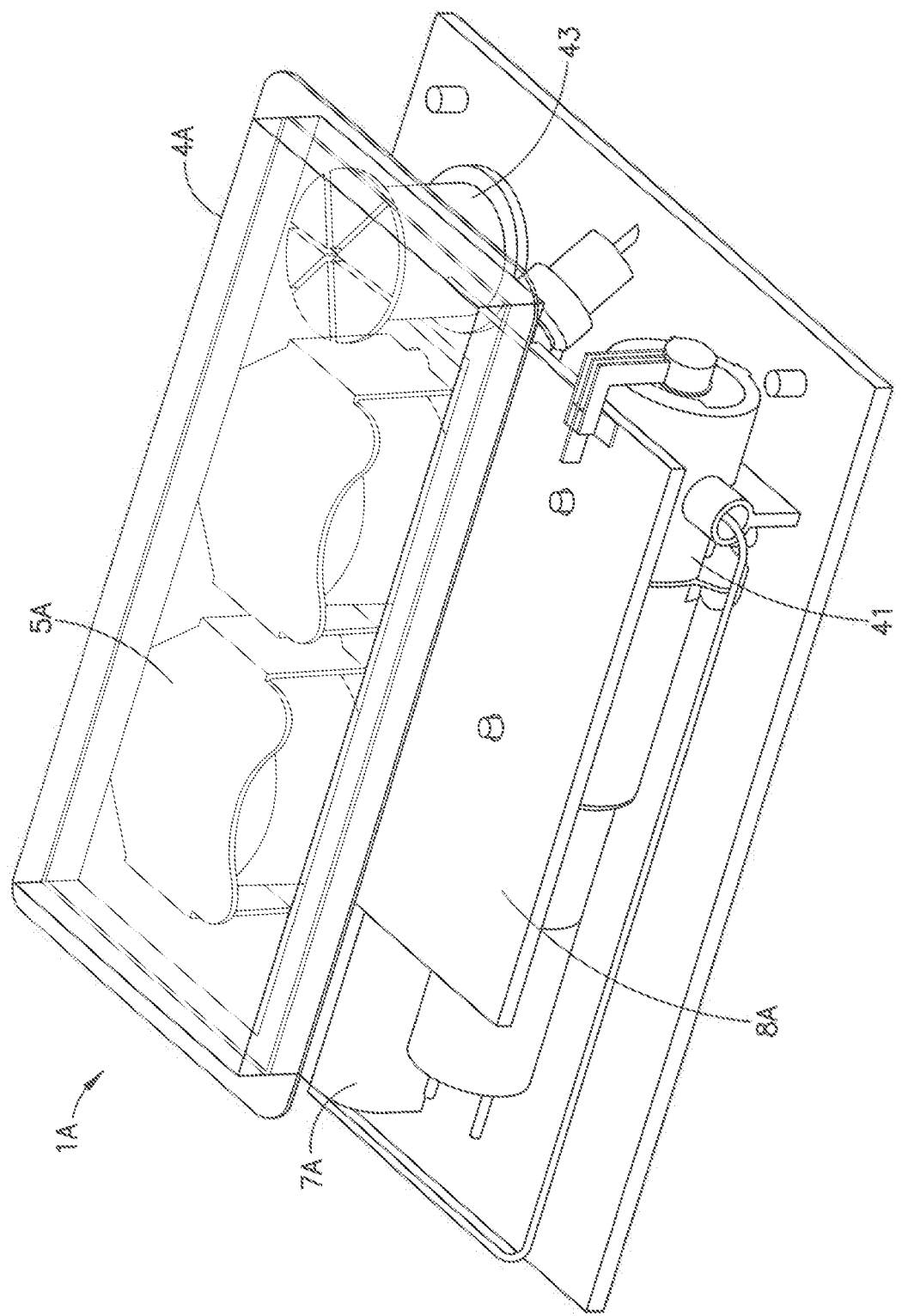
FIG. 3 is a perspective view of an alternative design for a patch pump having a flexible reservoir, illustrated without a cover.

FIG. 3 is a perspective view of an alternative design for a patch pump 1A having a flexible reservoir 4A, and illustrated without a cover. Such arrangement may further reduce the external dimensions of the patch pump 1A, with the flexible reservoir 4A filling voids within the patch pump 1A. The patch pump 1A is illustrated with a conventional cannula insertion device 7A that inserts the cannula, typically at an acute angle, less than 90 degrees, at the surface of the user's skin. The patch pump 1A further comprises: a power source 5A in the form of batteries; a metering sub-system 41 that monitors the volume of insulin and includes a low volume detecting ability; control electronics 8A for controlling the components of the device; and a reservoir fill port 43 for receiving a refill syringe 45 to fill the reservoir 4A.

Figure 4:
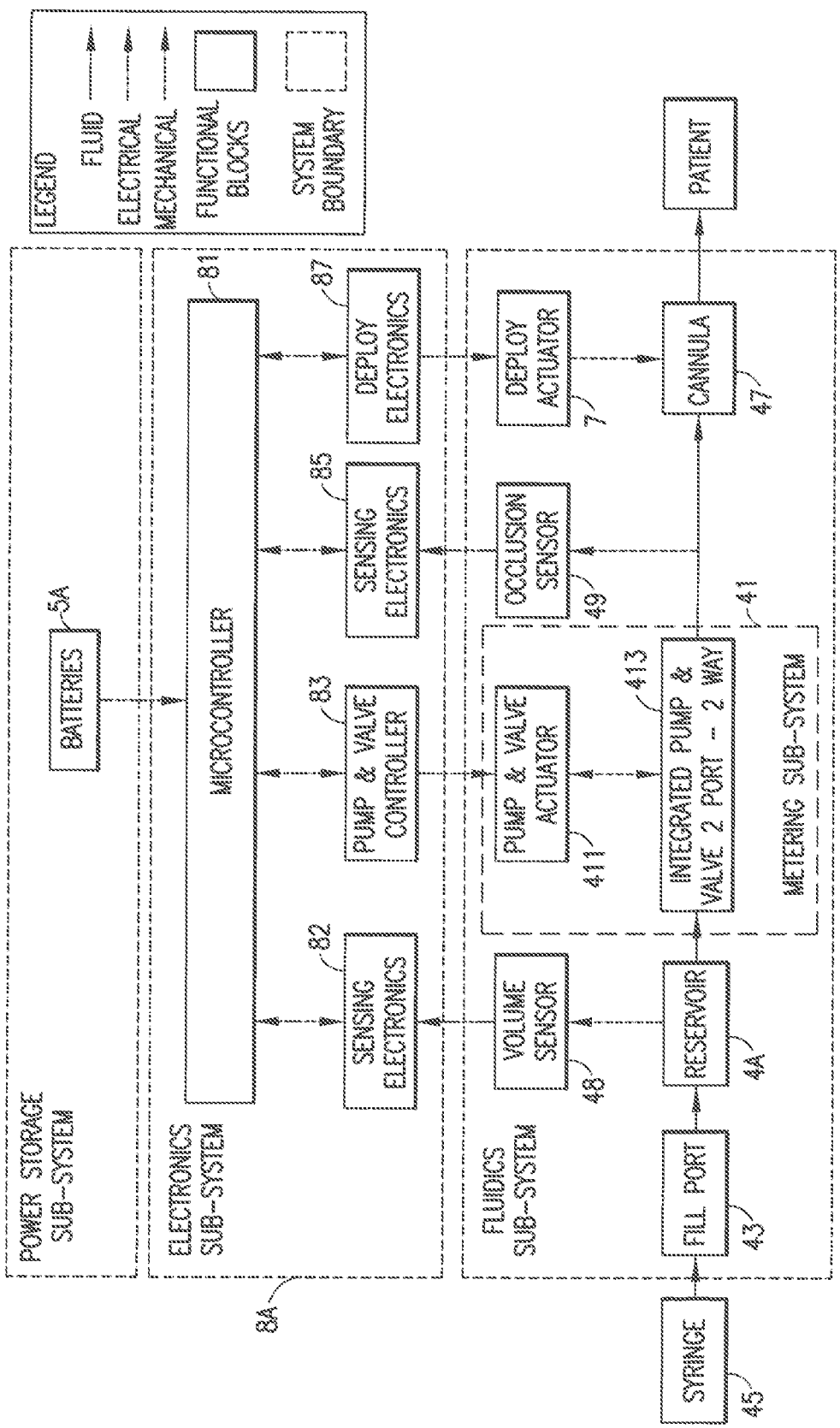
FIG. 4 is a patch-pump fluidic architecture and metering sub-system diagram of the patch pump of FIG. 3.
Figure 5:
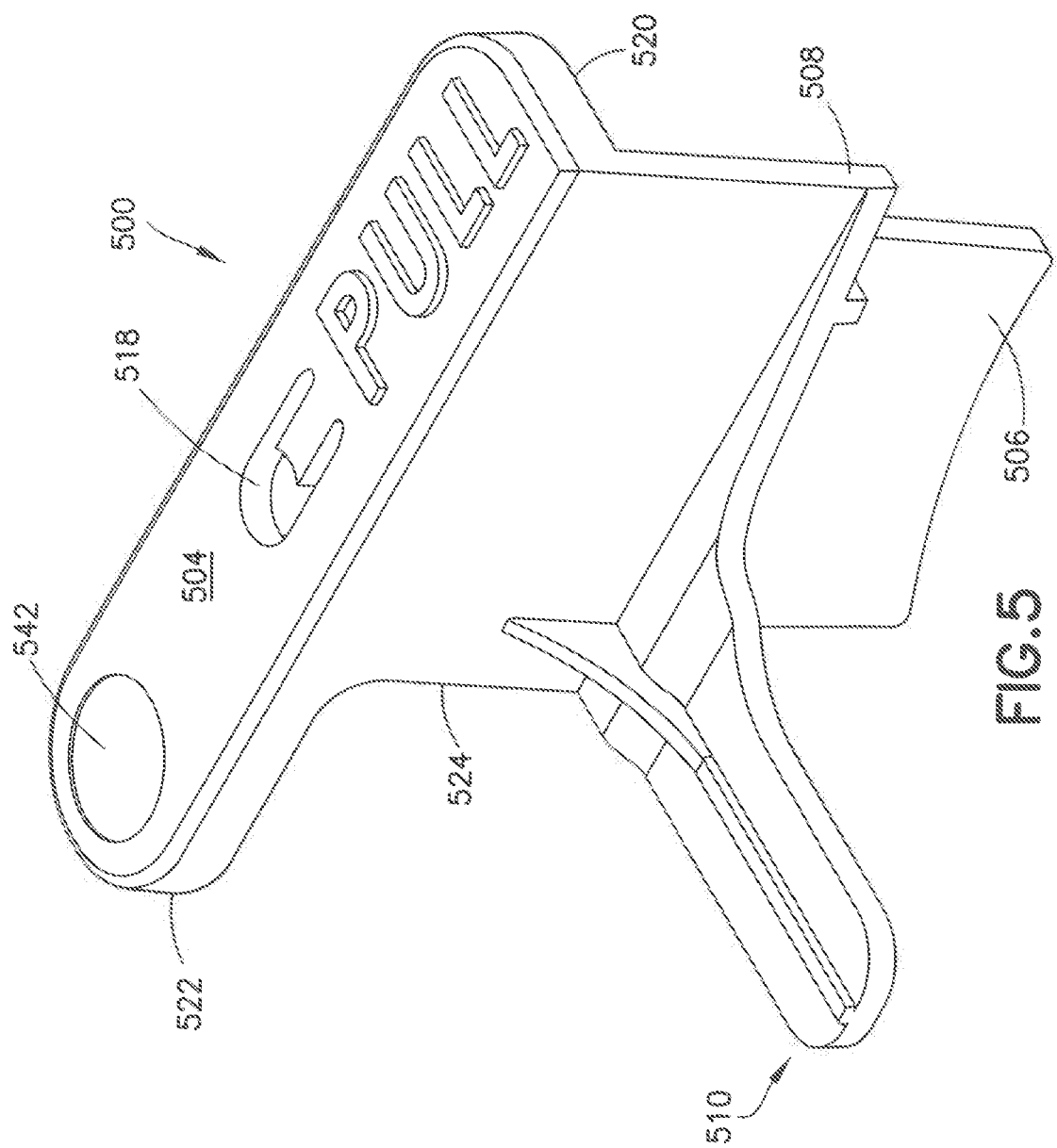
FIG. 5 is a front perspective view of a button safety cap according to an illustrative embodiment of the present invention.

FIG. 4 is a patch-pump fluidic architecture and metering sub-system diagram of the patch pump 1A of FIG. 3. The power storage sub-system for the patch pump 1A includes batteries 5A. The control electronics 8A of the patch pump 1A may include a microcontroller 81, sensing electronics 82, pump and valve controller 83, sensing electronics 85, and deployment electronics 87 that control the actuation of the cannula insertion mechanism. The patch pump 1A includes a fluidics sub-system that may include a reservoir 4A, volume sensor 47 for the reservoir 4A, a reservoir fill port 43 for receiving a refill syringe 45 to refill the reservoir 4A. The fluidics sub-system may include a metering system comprising a pump and valve actuator 411 and an integrated pump and valve mechanism 413. The fluidics sub-system may further include an occlusion sensor, a deploy actuator, as well as the cannula 47 for insertion into an infusion site on the user's skin. The architecture for the patch pumps of FIGS. 1 and 2 is the same or similar to that which is illustrated in FIG. 4.

Embodiments of the present invention include a button safety cap to prevent accidental activation of a catheter insertion mechanism of a patch pump and to stabilize the device while the user is filling a reservoir of the patch pump. The embodiment described herein is particularly adapted to work with the insertion mechanism described in further detail in PCT Patent Application No. PCT/US15/27367, but it should be readily appreciated by those of ordinary skill in the art that with modifications to the particular configuration of the button safety cap, embodiments of the present invention can be adapted to work with any insertion mechanism having a button. Embodiments of the present invention can work with patch pumps having cannula insertion mechanisms that use a rigid needle to drive a soft cannula into the skin of a user, and then retract the rigid needle leaving the soft cannula in the skin, and may also work with insertion mechanisms that utilize a rigid indwelling needle.

Accidental activation can cause needle stick injury, so it is desirable to provide a button safety device that prevents such injuries. If the insertion mechanism were to be accidentally activated before being placed on the skin, the patch pump would no longer be usable if the catheter insertion mechanism cannot be reset. If the reservoir was filled before the accidental activation, the insulin would also be wasted.

Figure 14:
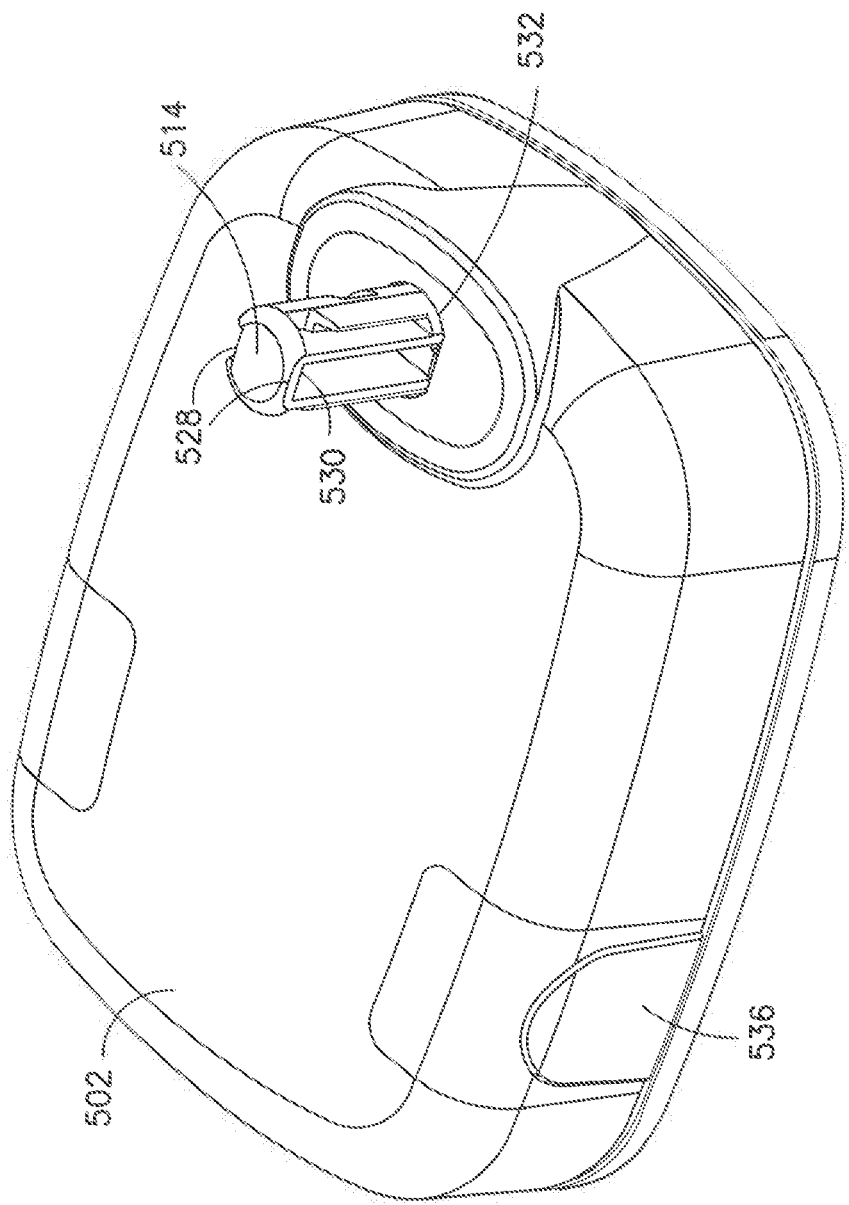
FIG. 14 is a perspective view of the illustrative fluid infusion device in FIG. 12 without the adhesive layer and liner and with its insertion mechanism in a non-deployed position.
Figure 15:
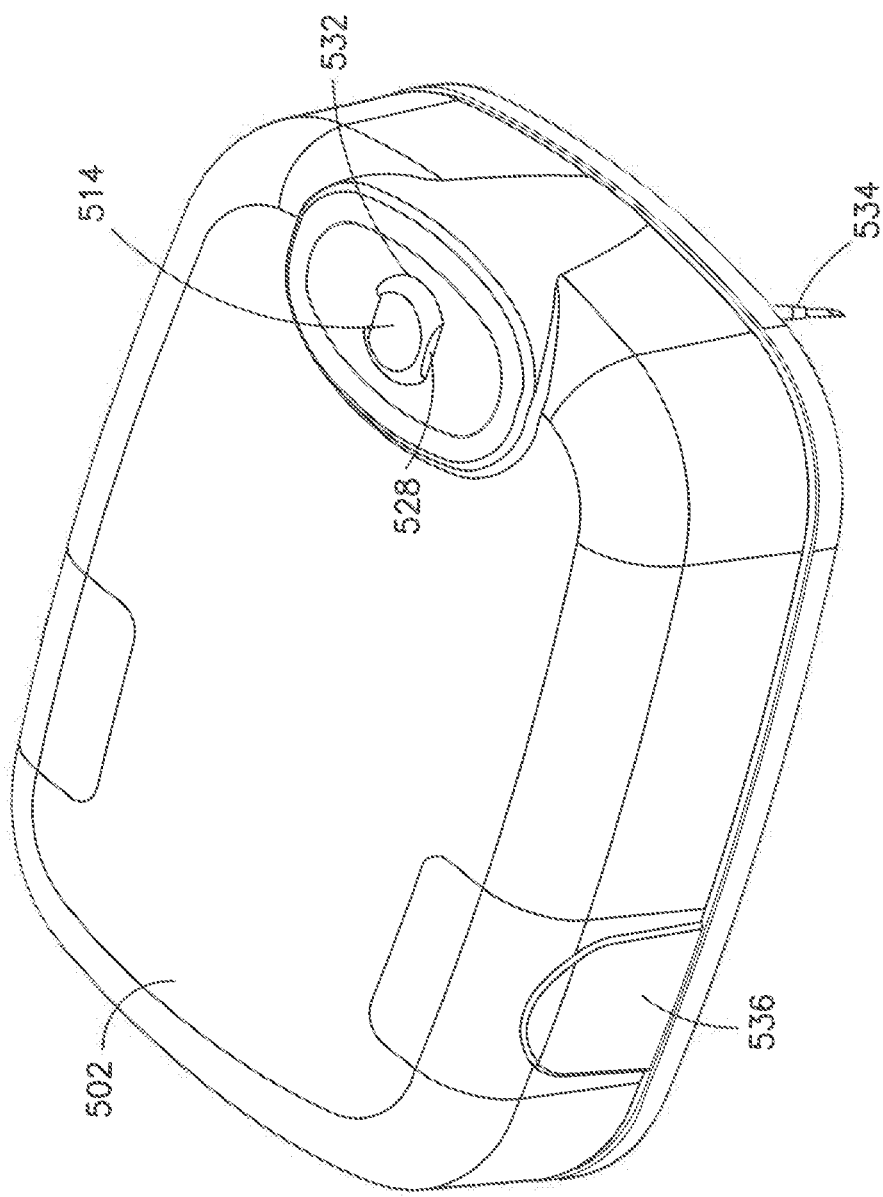
FIG. 15 is a perspective view of the illustrative fluid infusion device in FIG. 14 with its insertion mechanism in a deployed position.

Without a button safety, accidental activation could occur by the user accidentally pushing the button while handling the device before it is placed on the skin. The insertion mechanism described in PCT Patent Application No. PCT/US15/27367 has a feature that prevents the needle from being exposed from the bottom of the medication delivery device when a small amount of force is applied but, if a force higher than that threshold is accidentally applied, the user could be injured by the introducer needle. With reference to FIGS. 14 and 15, if the insertion mechanism activation button 514 was pushed all the way down before the device 502 was adhered to the body, the catheter 534 would lock in the distal position as shown in FIG. 15, and the introducer needle would retract thus rendering the insertion mechanism unusable. If the button 514 was pushed with enough force to surpass the minimum threshold force but not pushed the full stroke length, the introducer needle would be exposed and possibly be injuring the user but the needle and catheter would retract back into the device. In this scenario, the insertion mechanism would be reset and could be used to insert the catheter into the skin.

Figure 12:
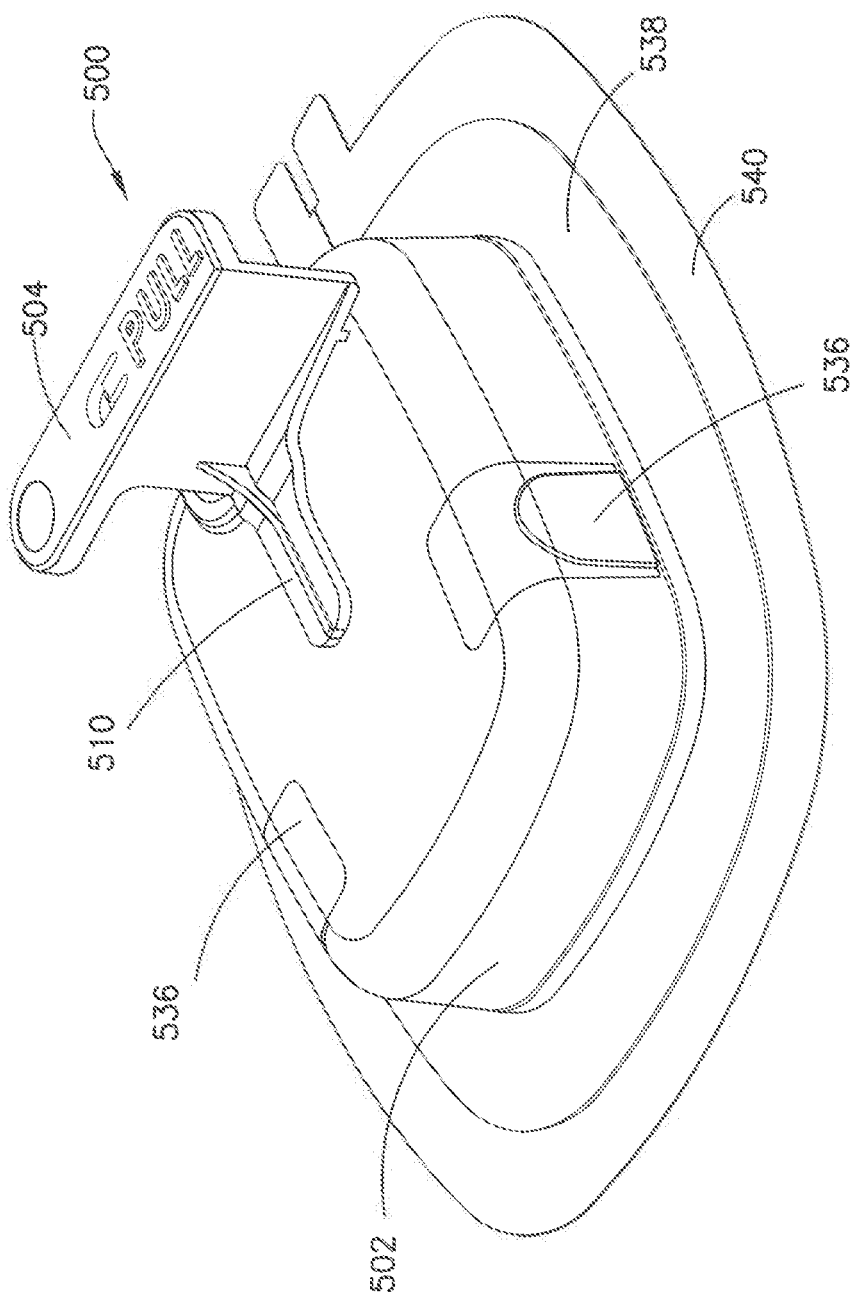
FIG. 12 is a perspective view of a button safety cap deployed on an illustrative fluid infusion device with adhesive layer and liner according to an illustrative embodiment of the present invention.
Figure 13:
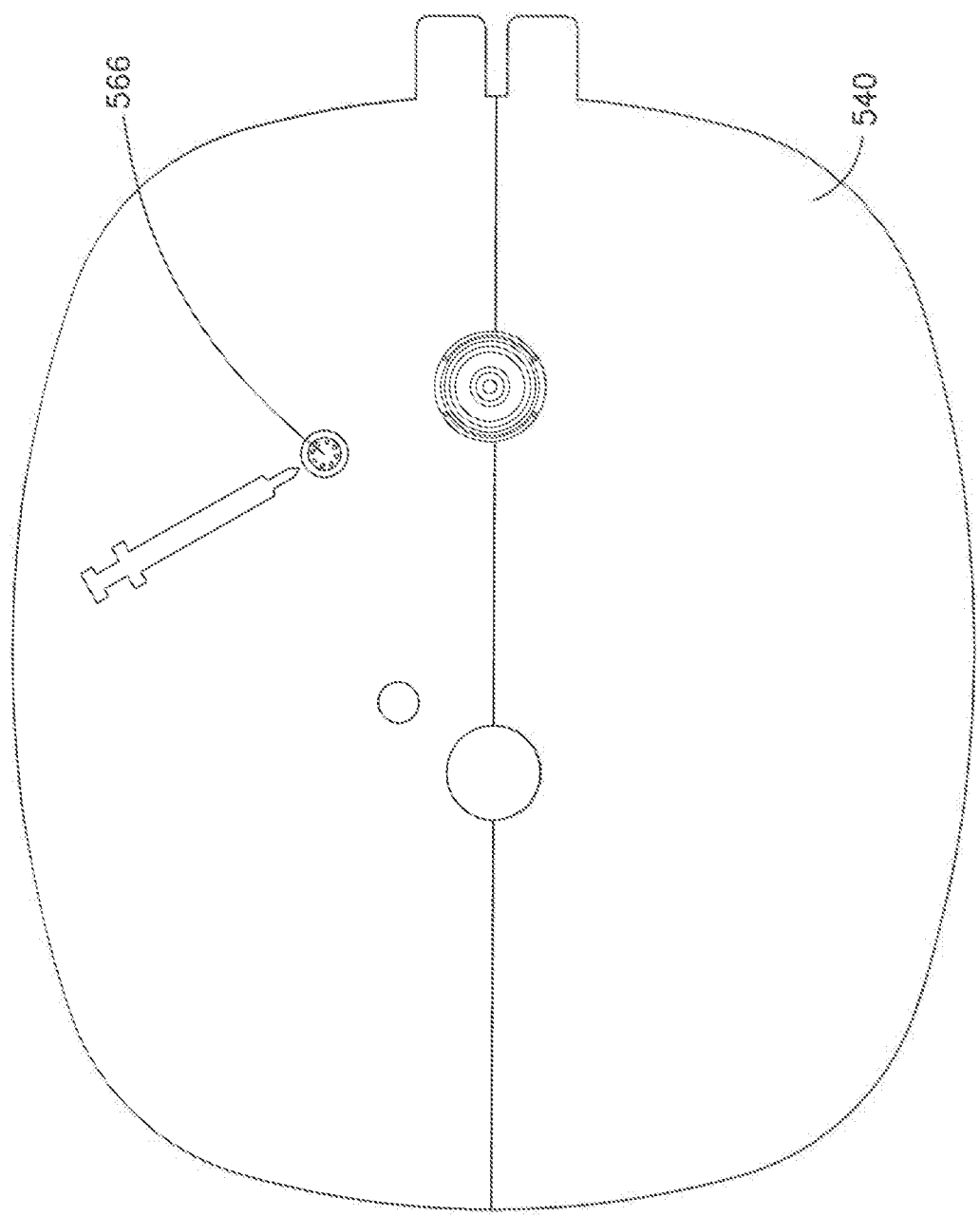
FIG. 13 is a bottom view of the fluid infusion device with adhesive layer and liner in FIG. 12.

The insertion mechanism activation button 514 can be accidentally activated during the reservoir fill step. With reference to FIGS. 12 and 13, the reservoir fill port is typically on the opposite side of the device 502 as the insertion mechanism activation button 514. The user inserts a syringe needle through the fill port septum 566 and injects the contents of the syringe to fill a reservoir in the device 502. If the device was placed with the fill port facing up on a surface, then without a button safety cap the device would rest on the insertion mechanism activation button 514. If the device 502 is pushed downwards with sufficient force, the insertion mechanism can activate and be deployed as illustrated in FIG. 15. Pushing the syringe plunger to fill the reservoir could cause this to occur.

Figure 8:
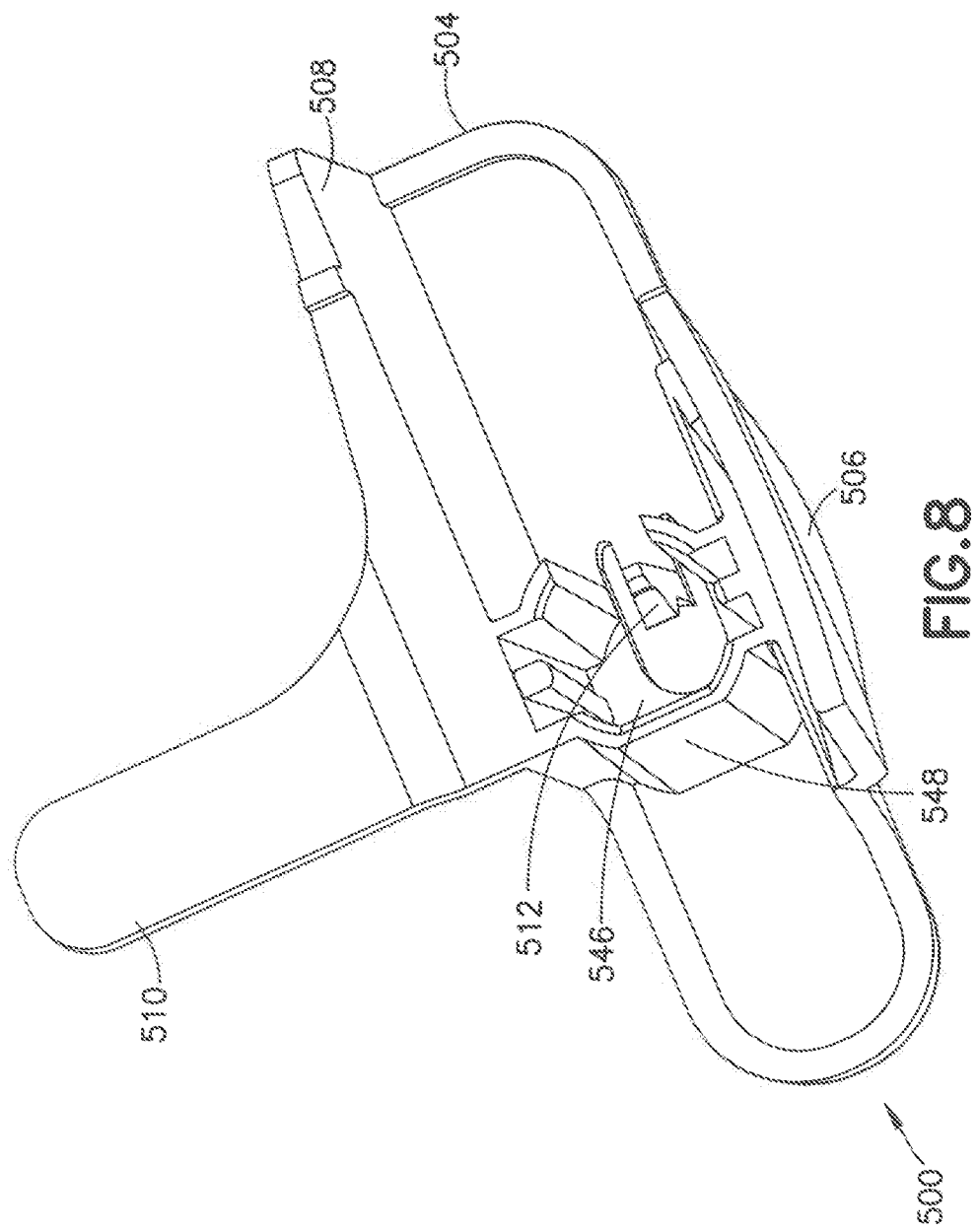
FIG. 8 is a bottom perspective view of a button safety cap according to an illustrative embodiment of the present invention.
Figure 9:
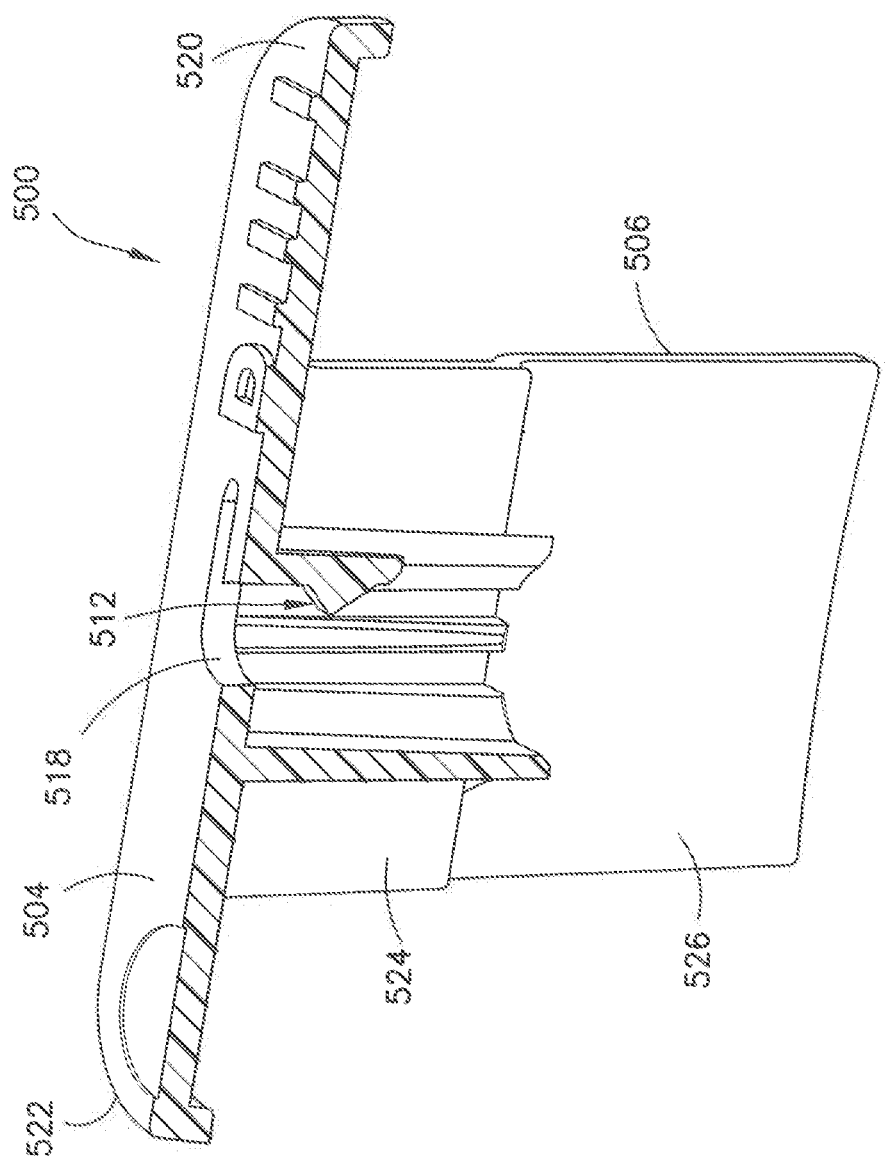
FIG. 9 is a cross-section view of a button safety cap in FIG. 7.
Figure 10:
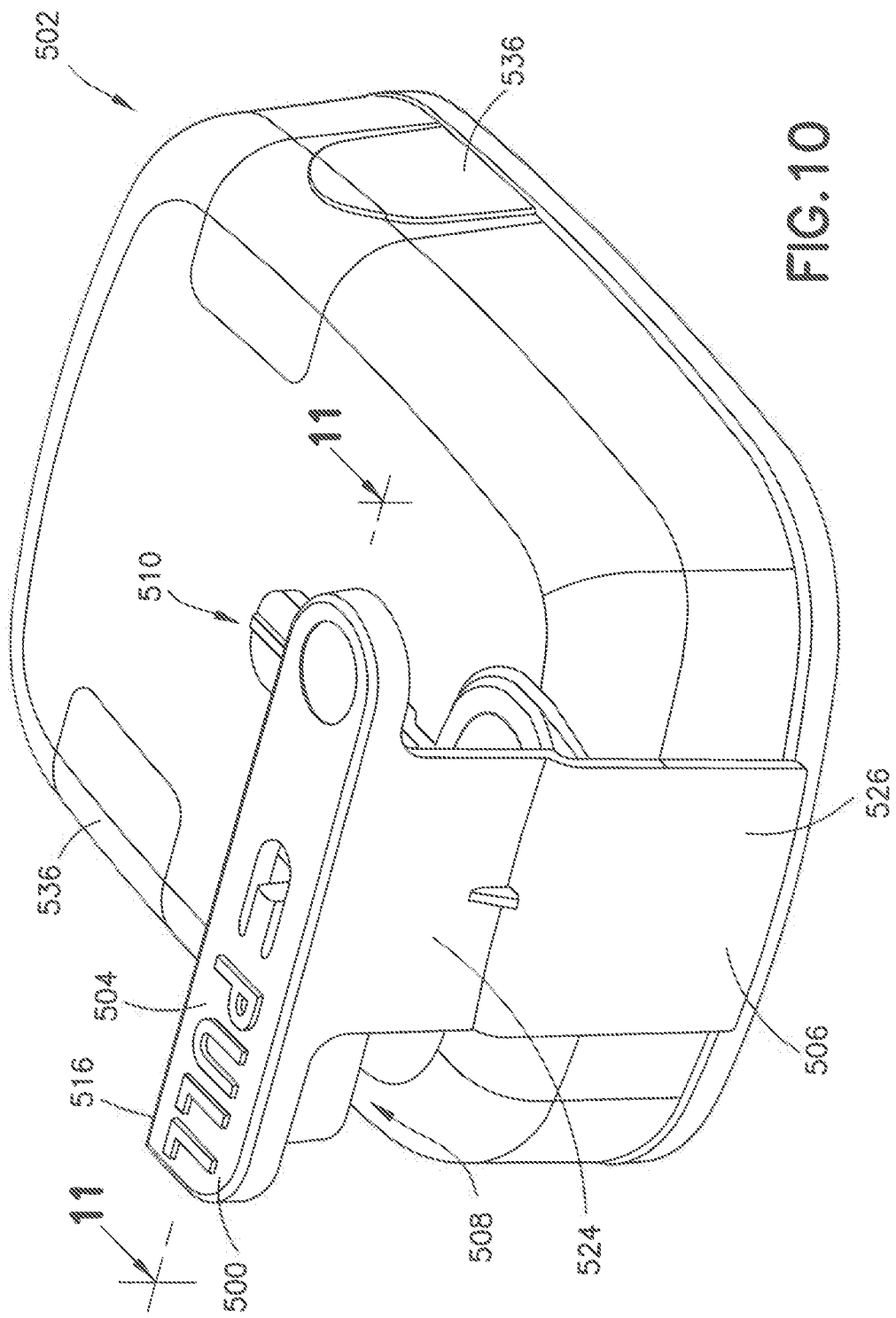
FIG. 10 is a perspective view of a button safety cap deployed on an illustrative fluid infusion device according to an illustrative embodiment of the present invention.
Figure 11:
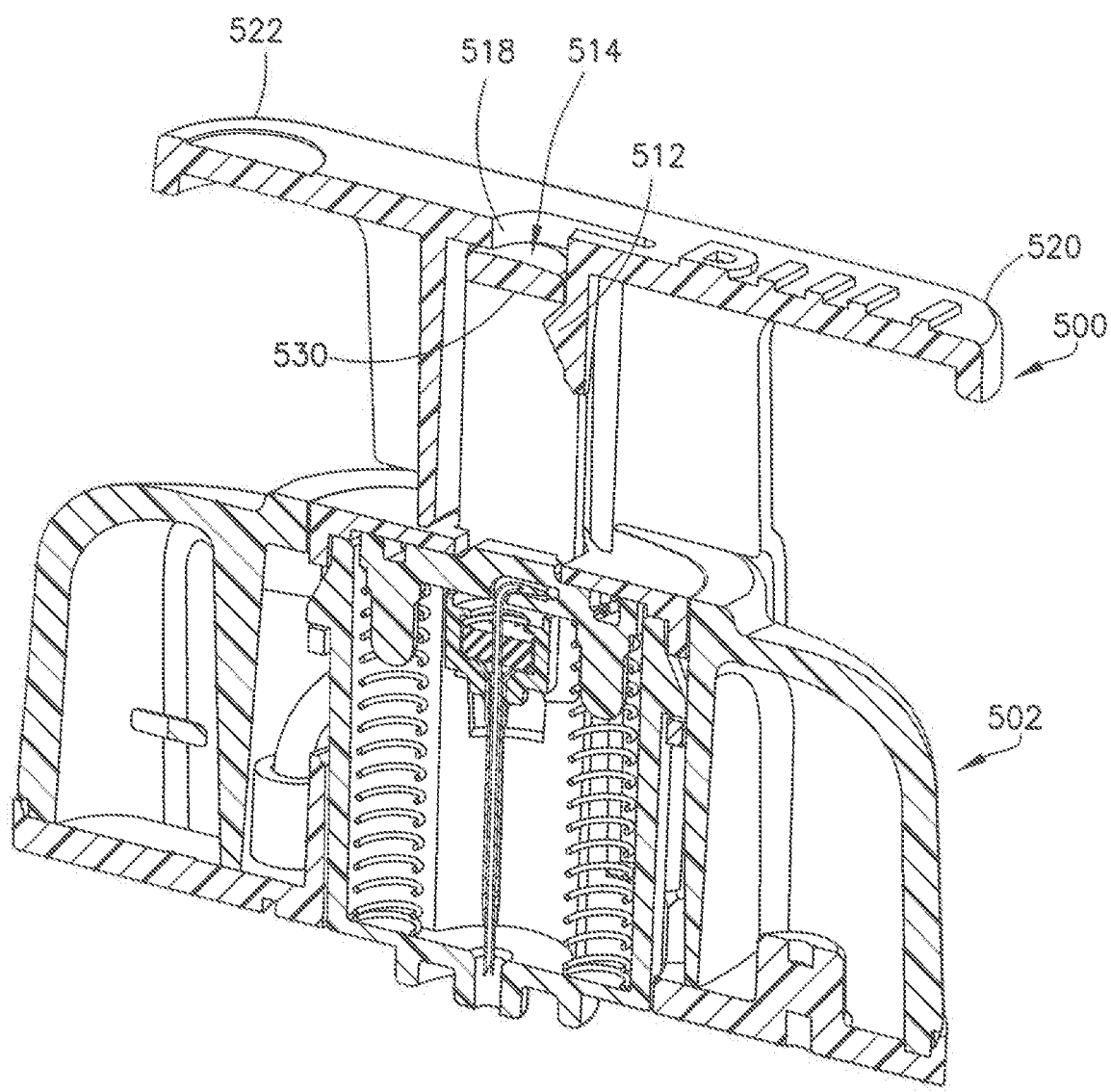
FIG. 11 is a cross-section view of the button safety cap and fluid infusion device in FIG. 10.

FIGS. 5, 6, 7, 8, 9 and 16 illustrate a button safety cap 500 according to an illustrative embodiment of the invention. FIGS. 10, 11 and 12 illustrate the button safety 500 installed onto a patch pump 502. Patch pump 502 is preferably manufactured with the button safety cap 500 assembled onto the patch pump 502. When installed on the patch pump 502, the button safety cap 500 covers the pre-activation insertion mechanism activation button 514 to prevent accidental activation. The button safety cap 500 is preferably, but not necessarily, a single molded part constructed of a rigid but flexible material such as plastic.

Figure 6:
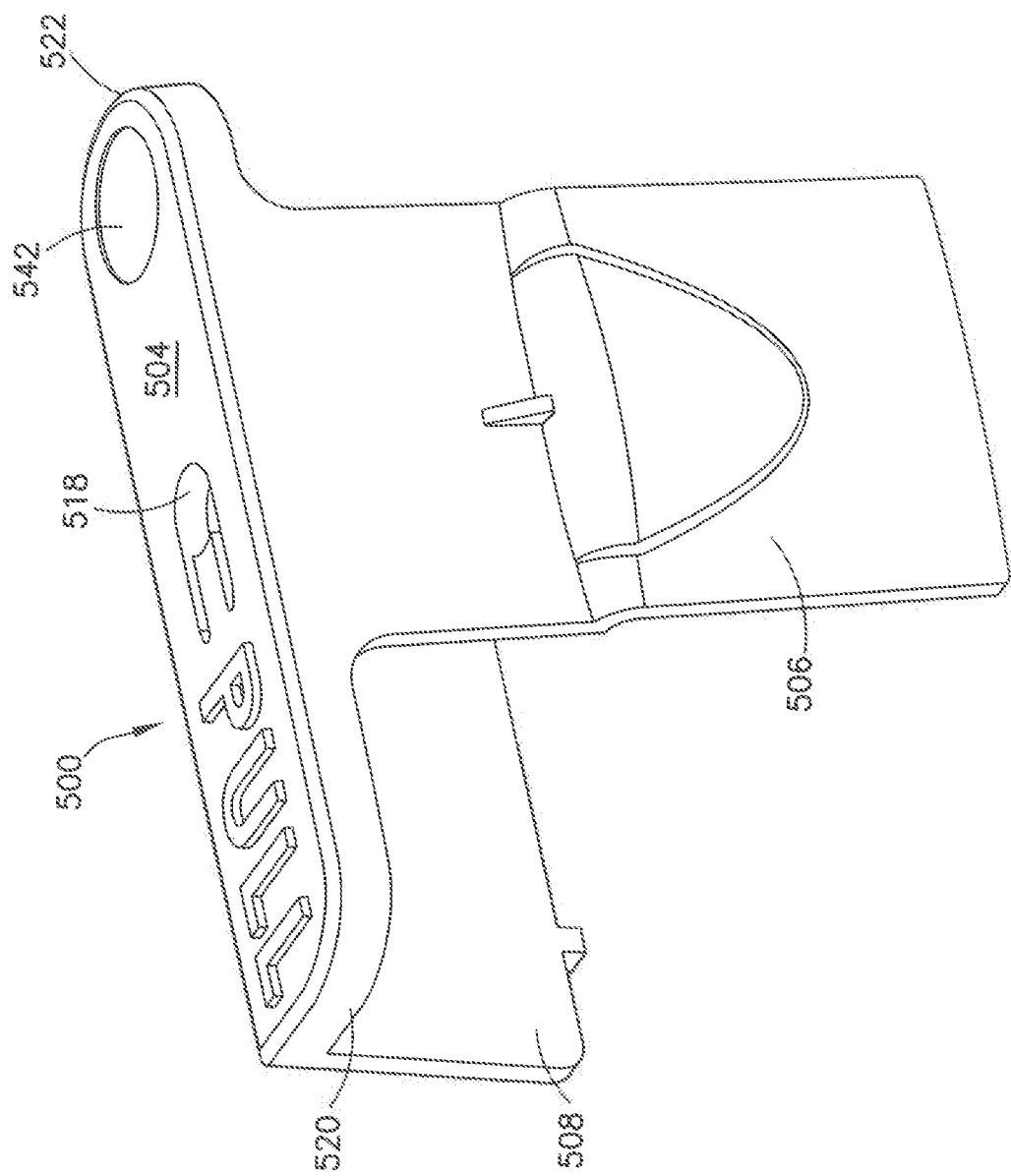
FIG. 6 is a back perspective view of a button safety cap according to an illustrative embodiment of the present invention.
Figure 7:
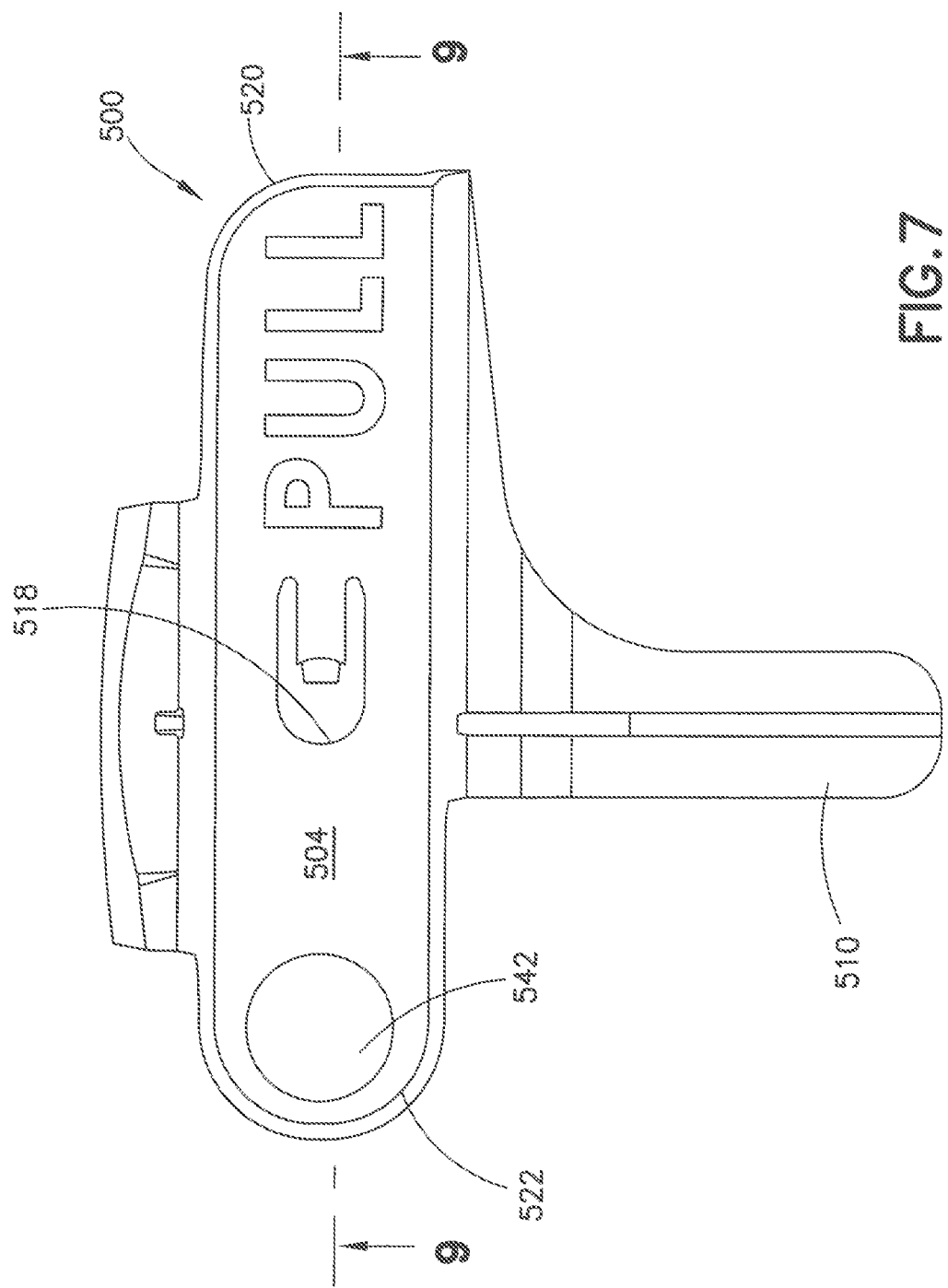
FIG. 7 is a top view of a button safety cap according to an illustrative embodiment of the present invention.

As illustrated, the button safety cap 500 includes a pull member 504 that the user may pull to remove the button safety cap 500 from the patch pump when the user is ready to activate the catheter insertion mechanism (e.g., via a button 514). Button safety cap 500 also preferably includes a contoured surface 506 to stabilize the button safety cap on the patch pump 502 housing. With reference to FIGS. 6, 9 and 10, the surface 506 of the button safety cap 500 is contoured along a side of the pump 502 and therefore vertical axis of the pump that is parallel to longitudinal axis of button 514 for increased stabilization of the button safety cap 500 relative to the pump. The button safety cap 500 can also include stabilizing arms 508 and 510 disposed, respectively, along transverse and longitudinal axes of the pump 502 for increased stabilization of the button safety cap 500 relative to the pump 502.

The height dimension of the button safety cap 500 (e.g., combined dimension of the arm 508 that extends along the vertical axis of the pump and the thickness of the pull 504) is configured to accommodate the insertion mechanism at its full pre-deployment position as illustrated in FIG. 14. The insertion mechanism can be damaged if its activation button 514 is torqued with enough force. Contoured surface 506 and stabilizing arms 508 and 510 constrain the button safety cap 500 on the patch pump 502 to prevent rotation or translation in directions that could damage the device or torque the insertion mechanism activation button 514.

FIGS. 8, 9 and 11, the pull member 504 has a cutout 518 with a snap feature 512. The snap feature 512 is configured to extend partially across the cutout 518 to provide some flexibility to the snap feature 512. As shown in FIG. 11, the snap feature 512 is also configured to extend along the parallel and respective vertical axis of the pump 502 and longitudinal axis of its insertion mechanism activation button 514. The snap feature 512 has an angled surface that engages a surface or edge 530 of the button 514 to provide some tension to retain the button safety 500 cap on the button 514 but to release the cap 500 from the button 514 upon the application of a designated amount of force on the pull member 504 corresponding to when the user wishes to remove the cap 500 from the button 514 and depress the button 514 to deploy the insertion mechanism.

FIG. 9 is a cross-sectional view of the button safety cap 500, showing the snap feature 512. FIG. 11 is a cross-section of the button safety cap 500 assembled onto the patch pump 502. As shown in FIG. 11, snap feature 512 locks the button safety cap 500 onto insertion mechanism activation button 514 until sufficient force is used to overcome the predetermined deformation force required to disengage snap feature 512 from the surface or edge 30 of the insertion mechanism activation button 514. In this manner, the button safety 500 is held onto the patch pump 502 until intentionally removed by the user. The snap feature 512 is preferably designed to disengage from the activation button 514 when excessive torque is applied around the activation button 514 primary axis in order to prevent damage to the insertion mechanism.

Figure 16:
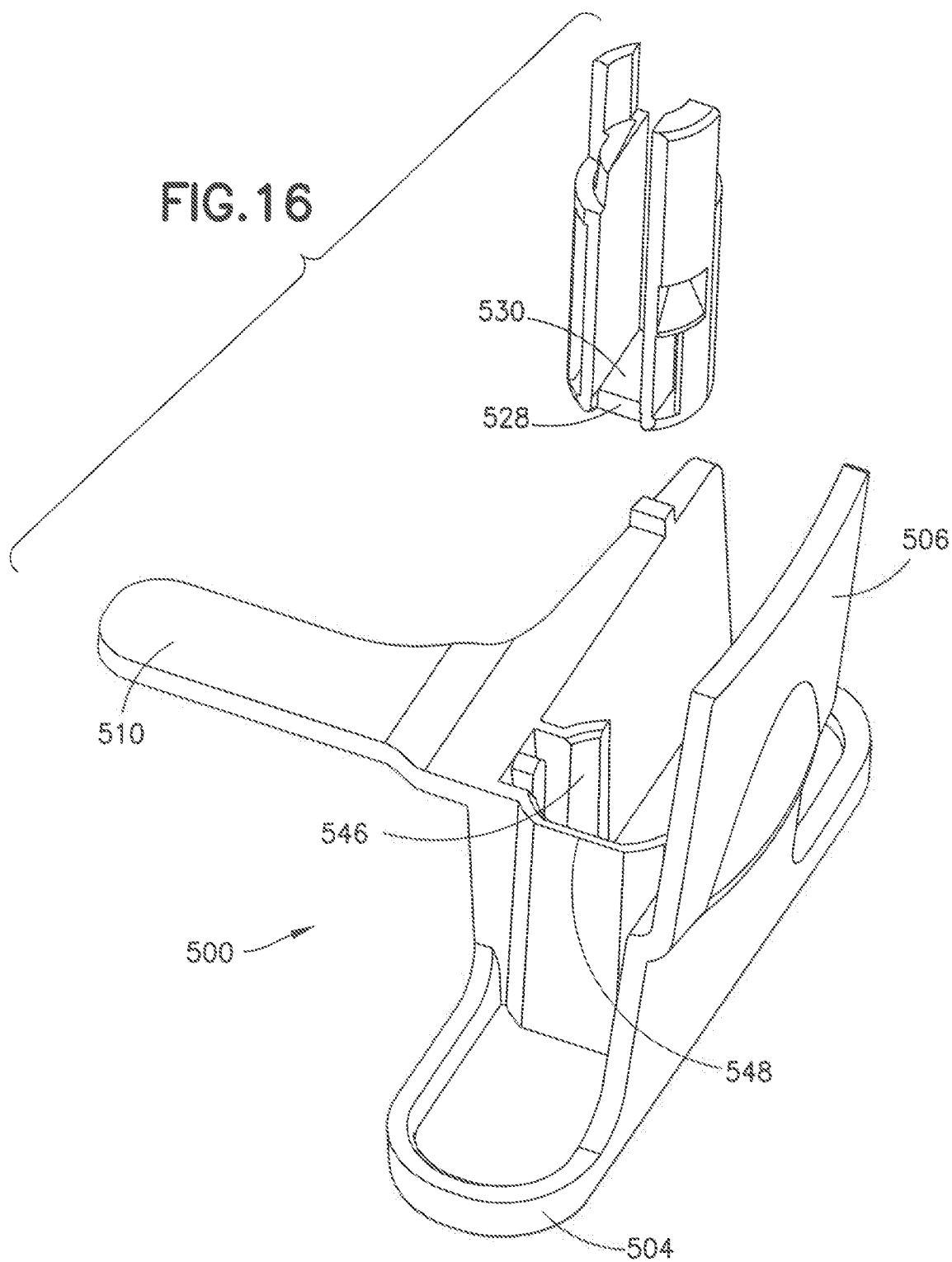
FIG. 16 is an exploded view of part of the insertion mechanism in FIG. 14 aligned for engagement with the bottom of the button safety cap according to an illustrative embodiment of the present invention.

The shape of the insertion mechanism activation button 514 can be configured with opposing flat sides 528 as illustrated in FIGS. 14, 15 and 16 to facilitate assembly and prevent rotation of the insertion mechanism activation button 514 in an aperture 532 in the device 502 housing through which insertion mechanism activation button 514 deploys. In addition, the button safety cap 500 comprises a cavity 546 with a corresponding shape to match the circumference of the button 514 such that the button safety cap 500 and button 514 can be assembled without rotational motion that could damage the insertion mechanism and make assembly more difficult.

With reference to FIGS. 8 and 16, the underside of the button safety cap 500 has a cavity 546 that is dimensioned to receive the insertion mechanism activation button 514 when in its undeployed position (e.g., see FIG. 14). As stated above, the insertion mechanism activation button 514 can have opposing flat surfaces or sides 528. One of the flat surfaces or sides 528 comprises the surface or edge 530 that engages the snap feature 512 to retain the button safety cap 500 on the button 514 until the cap 500 is intentionally removed from the button 514 by a user. The button safety cap 500 has a corresponding mating flat surface 548 that abuts the other one of the flat surfaces or edges 528 of the button 514 to constrain the button in the assembled state.

Turning back to FIG. 6, the button safety 500 pull member 504 is preferably elongated and includes an edge 516 that makes contact with a flat surface when the patch pump is turned over by a user to fill the reservoir port located on the bottom of the patch pump housing. Edge 516 stabilizes the patch pump while resting upside-down on a surface for reservoir filling. In this manner, reservoir filling is made easier for the user, and at the same time the button safety 500 prevents accidental activation of the activation button 514 while the user is potentially pressing down on the patch pump while it is turned over.

Further, the pull member 504 can be dimensioned and shaped to optimize ergonomics of the user's hand and particularly the action of the thumb and fingers on the user's hand to make removal of the button safety cap 500 convenient and with an efficient user motion. As illustrated, the pull member 504 has ends 520 and 522. The width of the contour surface 506 (i.e., the dimension of contour surface 506 along the transverse axis of the pump 502) and the spacing of the contour surface 506 along the pull member 504 relative to its ends 520 and 522 can accommodate, for example, the thumb and index finger of the user's right hand at one end 522 and one or more of user's finger pads at other end 520 to facilitate grip, as well as encourages lift of the cap 500 without torquing the button 514. The dimensions and shapes of the ends 520 and 522 of the pull member 506 and the surface area of the pull member 504 can be configured to accommodate different user hand and finger ergonomics, depending on where insertion mechanism and therefore button safety cap 500 are deployed on the medication delivery device (e.g., pump 502).

While various embodiments have been shown and described, it will be understood by those skilled in the art that various changes and modifications can be made without departing from the scope of the invention as defined in the appended claims.

What is claimed is:

1. A fluid infusion device comprising:
   a housing configured to be worn by a user that comprises a first side, and a second side opposite to the first side, the housing configured to be adhered to the user's skin when the housing is worn by the user;
   a cannula insertion mechanism, the cannula insertion mechanism comprising an insertion mechanism activation button configured to extend from the first side of the housing of the fluid infusion device in an undeployed position and, when pressed toward the housing into a deployed position, to introduce a cannula and/or the needle into the user's skin from the second side of the housing for placement of the cannula and/or needle during wearing of the housing by the user;
   a pump in the housing, the pump being configured to provide fluid from a reservoir to the user via a flow path and the cannula and/or the needle;
   a button safety cap assembled onto the insertion mechanism activation button when in the undeployed position and comprising:
      a pull member;
      at least one stabilizing arm adapted to prevent rotation and/or translation of the button safety cap relative to at least one of the activation button and the fluid infusion device; and
      a flexible snap feature adapted to engage the activation button;
      wherein the snap feature retains the button safety cap on the activation button until a predetermined removal force is applied to the button safety cap.

2. The fluid infusion device of claim 1, wherein the pull member comprises a flat stabilizing edge adapted to rest on a flat surface on which the fluid infusion device is oriented during filling of the reservoir via a reservoir port of the infusion device.

3. The fluid infusion device of claim 1, wherein the snap feature disengages from the insertion mechanism activation button if a predetermined torque is applied to the button safety cap.

4. The fluid infusion device of claim 1, wherein the at least one stabilizing arm comprises a first stabilizing arm having a first surface extending between the pull member and an external surface of the fluid infusion device, the first surface and the pull member being dimensioned to receive the insertion mechanism activation button before it has been deployed to the deployed position, and to extend along a transverse axis of the fluid infusion device.

5. The fluid infusion device of claim 4, wherein the at least one stabilizing arm comprises a second stabilizing arm extending from the first surface and along a longitudinal axis of the fluid infusion device.

6. The fluid infusion device of claim 1, further comprising a contour surface extending from the pull member and along a side of the fluid infusion device.

7. The fluid infusion device of claim 1, wherein the button safety cap further comprises a cavity configured to receive the insertion mechanism activation button in its undeployed position.

8. The fluid infusion device of claim 7, wherein the insertion mechanism activation button has opposing flat surfaces extending along a portion of its longitudinal axis, and the cavity is configured to have respective flat surfaces that abut the flat surfaces of the insertion mechanism activation button when the button safety cap engages with the insertion mechanism activation button.

9. The fluid infusion device of claim 7, wherein a height of the cavity relative to the first side of the housing is dimensioned to receive a length of the insertion mechanism activation button extending from the housing when in its undeployed position.

\* \* \* \* \*